(12) United States Patent
Biskupski et al.

(10) Patent No.: US 9,068,924 B2
(45) Date of Patent: Jun. 30, 2015

(54) GAS SENSOR

(71) Applicants: Diana Biskupski, Bayreuth (DE);
Maximilian Fleischer, Höhenkirchen (DE); Ralf Moos, Bayreuth (DE);
Daniela Schönauer, Heinersreuth (DE);
Kerstin Wiesner, Putzbrunn (DE)

(72) Inventors: Diana Biskupski, Bayreuth (DE);
Maximilian Fleischer, Höhenkirchen (DE); Ralf Moos, Bayreuth (DE);
Daniela Schönauer, Heinersreuth (DE);
Kerstin Wiesner, Putzbrunn (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 0 days.

(21) Appl. No.: 13/895,474

(22) Filed: May 16, 2013

(65) Prior Publication Data
US 2013/0285682 A1 Oct. 31, 2013

Related U.S. Application Data

(62) Division of application No. 12/747,034, filed as application No. PCT/EP2008/066486 on Dec. 1, 2008, now abandoned.

(30) Foreign Application Priority Data

Dec. 10, 2007 (DE) .......................... 10 2007 059 653

(51) Int. Cl.
*G01N 27/406* (2006.01)
*G01N 27/16* (2006.01)
*G01N 27/407* (2006.01)

(52) U.S. Cl.
CPC ........... *G01N 27/16* (2013.01); *Y10T 29/49117* (2015.01); *G01N 27/4075* (2013.01)

(58) Field of Classification Search
CPC . G01M 15/10; G01M 15/102; G01M 15/104; G01N 1/2252; G01N 27/16404–27/407; G01N 27/409; G01N 27/419; G01N 27/41; F01N 2560/00–2560/20
USPC ........................ 204/421–429; 73/23.31, 23.32
See application file for complete search history.

(56) References Cited

U.S. PATENT DOCUMENTS

| 4,298,573 A * | 11/1981 | Fujishiro ........................ 422/94 |
| 5,595,647 A * | 1/1997 | Hoetzel et al. ............. 205/784.5 |
| 5,605,612 A * | 2/1997 | Park et al. ...................... 204/429 |
| 5,635,628 A * | 6/1997 | Fleischer et al. ............. 73/31.06 |
| 2007/0170057 A1* | 7/2007 | Kobayashi et al. ........... 204/424 |

FOREIGN PATENT DOCUMENTS

WO WO 2007/115855 * 10/2007

OTHER PUBLICATIONS

Machine translation WO 2007/115855 run Nov. 26, 2012.*

* cited by examiner

*Primary Examiner* — Jennifer Dieterle

(57) ABSTRACT

A combined gas sensor includes a first electrode and a second electrode, wherein the first and second electrodes are connected via an ion-conducting material. The first electrode is covered, in part, by a first catalytically active material. Further, a resistive gas sensor formed by a third electrode is arranged such that the third electrode is in direct contact with the first catalytic material and is not in direct contact with the first electrode.

19 Claims, 4 Drawing Sheets

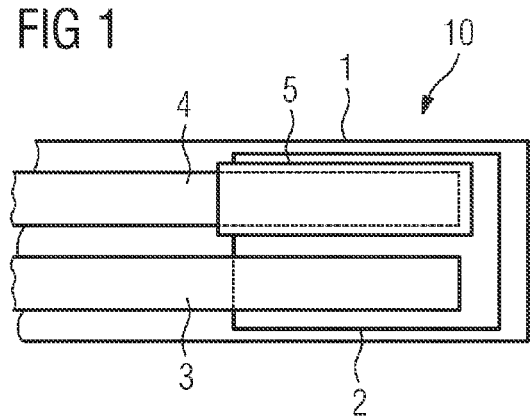
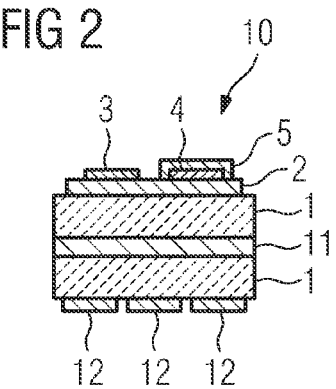
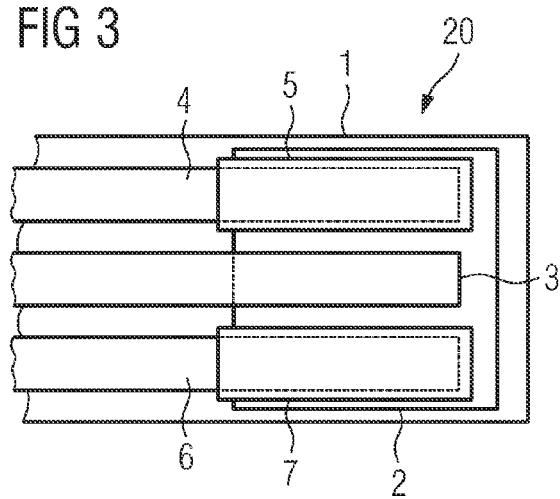
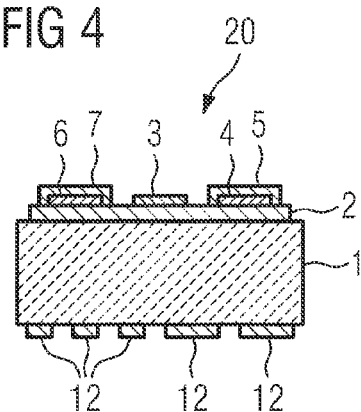

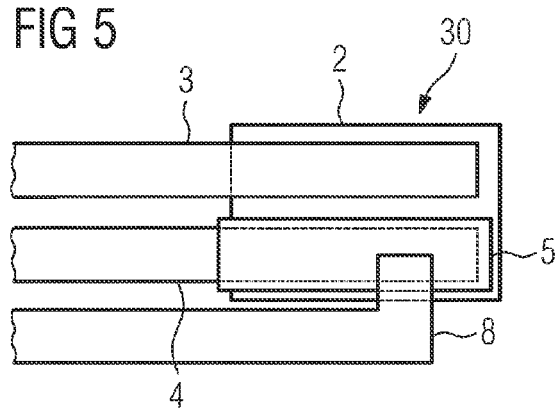
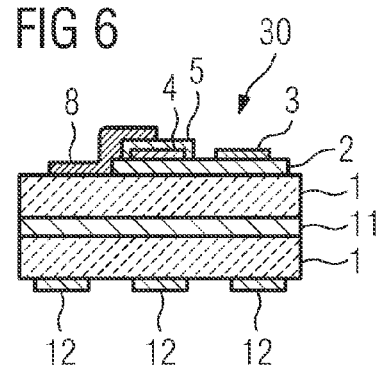
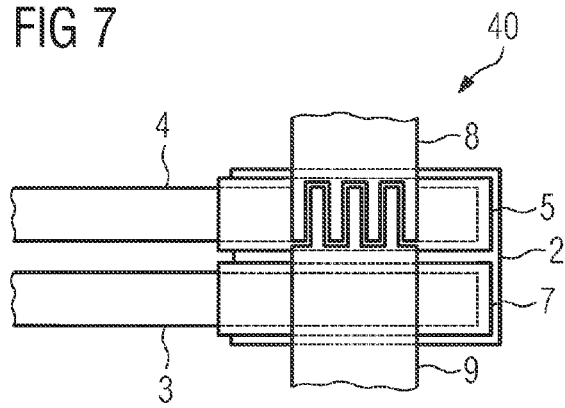
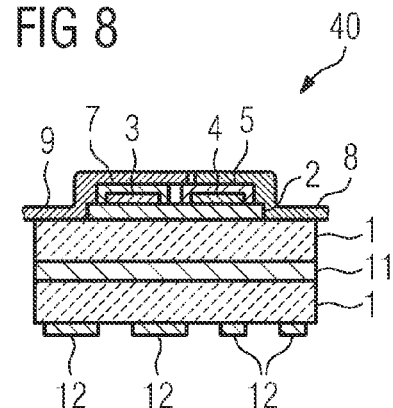

GAS SENSOR

CROSS REFERENCE TO RELATED APPLICATIONS

The present application is a divisional application of U.S. non-provisional application Ser. No. 12/747,034 filed Jun. 9, 2010, which is the US national stage of International application no. PCT/EP2008/066486 filed Dec. 1, 2008, and claims the benefit thereof. The International application claims priority to German application No. 10 2007 059 653.9 DE filed Dec. 10, 2007. All of the applications are incorporated by reference herein in their entirety.

FIELD OF INVENTION

An electrochemical gas sensor that comprises at least a first and at least a second electrode is provided. Further, a combined gas sensor, a method for producing and a method for operating an electrochemical gas sensor are provided.

BACKGROUND OF INVENTION

Nowadays gas sensors are used in many fields of technology in order to satisfy increasing demands placed on environmental compatibility and safety. One example of an application for gas sensors consists of detecting ammonia ($NH_3$) in the exhaust gas system of diesel engines. This may occur during selective catalytic reduction, or SCR, which is used to reduce the emission of nitrogen oxides ($NO_x$).

It is known to use 'mixed potential sensors' to detect ammonia in car exhaust gas systems. These electrochemical gas sensors have a first and a second electrode, the second electrode being made of a different material to the first electrode, which is in contact with the gas environment in which, for example, ammonia is to be detected. The two electrodes are connected via an ion-conducting, i.e. electrolytic material, for example, YSZ (yttrium-stabilized zirconium oxide). Depending on the gas concentration, an electromotive force (EMF), i.e. a voltage, is set between the electrodes. This is used as a measuring signal. In this case the second electrode is normally referred to as a passive electrode and is made, for example, of platinum. The first electrode is normally referred to as an active electrode and consists of a complex mixture of a metal oxide, for example bismuth vanadium oxide ($BiVO_4$), with an admixture of, for example, a metal such as 5% magnesium. In this case the complex material mixtures must satisfy a range of requirements. They must therefore be sufficiently electrically conductive. They must also be sufficiently thermally and chemically stable for the gas environments, which are often hot and aggressive, in which they will be used. Lastly, the complex material mixtures must be as catalytically selective as possible, i.e. they must promote as few chemical reactions as possible, ideally just one, in the gas environment to be measured. A drawback of known sensors is that their construction, in particular the construction of the complex first electrode, is very involved.

SUMMARY OF INVENTION

An object is to specify an electrochemical gas sensor and a method for the production thereof, with which simplified construction is made possible. An operating method affording an increased functional range will also be specified for a gas sensor of this type.

With regard to the electrochemical gas sensor the object is achieved by an electrochemical gas sensor having the features of the claims. With regard to the production method the object is achieved by a method having the features of the claims for producing an electrochemical gas sensor. With regard to the operating method the object is achieved by a method having the features of the claims for operating an electrochemical gas sensor. The dependent claims relate to embodiments and configurations.

The electrochemical gas sensor comprises a first and a second electrode. The two electrodes are connected via an ion-conducting material. The first electrode is covered, at least in part, by a first catalytically active material.

The electrochemical sensor is preferably based on the fact that it is known for an electromotive force (EMF), i.e. a voltage, to be set between the electrodes in the presence of catalytically oxidizable gases. The electrodes normally tap this voltage and it is therefore expedient for the electrodes to be sufficiently conductive.

Ion-conducting materials are also referred to as electrolytic materials. A solid electrolytic material is preferably used in the electrochemical sensor. Examples of this material include yttrium-stabilized zirconium oxide, also known as YSZ, or scandium-stabilized zirconium oxide (ScSZ).

In electrochemical gas sensors the electrodes are expediently not in direct contact with one another, but instead each contact the electrolyte so as to allow the voltage to be formed between the electrodes as a reaction to gases.

The sensors may be constructed in various possible ways for this purpose. The sensor is preferably formed in a planar manner. In this instance a substrate is preferably used. For example this may be an aluminum oxide lamina. Other possibilities consist of, for example, sapphire, quartz or silicon substrates. The substrate supports the other elements, i.e. at least the electrodes, the ion-conducting material and the catalytic layer, either directly or indirectly. These other elements are in turn formed as layers assembled on top of one another. A further possible construction consists of a non-planar construction. In an example of a construction of this type a spindle-shaped aluminum member supports the other elements. In this case the electrodes may, for example, be formed as wires that also act as suspension for the sensor. A substrate is also not always necessary. The electrodes or the ion conductor may therefore be configured in such a way that they support the electrochemical sensor.

The first electrode is covered, in part or completely, by a first catalytically active layer. The electrode is preferably covered in the region of the ion-conducting material. The catalytically active layer preferably, but not necessarily covers the first electrode completely in the region of the ion-conducting material.

In the method for producing the gas sensor an ion-conducting material is provided. The first and second electrodes are illustrated in conjunction with the ion-conducting material. Lastly, a first catalytic material is attached to the first electrode in such a way that the first electrode is covered by said material, at least in part. In this case the sequence of the steps is not important, the production process preferably being carried out in such a way that there are regions in the sensor at which the first catalytic material and the ion conductor meet and, at the same time, it is possible for gas to enter into these regions.

In the operating method for the electrochemical gas sensor a voltage is determined as a measuring signal between the first electrode and the second electrode.

It has been recognized that a problem of known electrochemical sensors comprising two electrodes is that an active electrode consisting of a complex material mixture is used in addition to an electrode commonly referred to as a passive electrode. This material mixture must therefore, on the one hand, be conductive enough to fulfill the function of the electrode and, on the other hand, be sufficiently chemically and thermally stable in the measuring environment. Production of these electrodes is complex and yet the electrodes, which consist for example of a mixture of a metal oxide, such as $BiVO_4$, with 5% Mg for example, do not exhibit optimal conductivity.

By contrast, a substantially simpler construction, and therefore simpler and more cost-effective production of the sensor is advantageously obtained if the aforementioned functions of the electrode are separated. The first electrode is therefore provided in conjunction with the first catalytically active material.

It is advantageously possible to combine a number of the sensors to form a sensor system, this system then possibly comprising a plurality of first and second electrodes. In this case redundant elements may advantageously be omitted and therefore only one substrate might be used in a planar construction or, for example, only one ion-conducting layer might be used for a plurality of electrodes. For example the system may be used to obtain more information about the gas composition or to identify identical information as redundant.

A first electrode that may also be referred to as an active electrode depending on the configuration of the sensor may therefore also be formed and is preferably more conductive over its entire extension than a known active electrode. At the same time it may be advantageous with regard to the first catalytically active material to resort to a material that, for example, is known from the field of car emission control or firing systems. In this case the specific electrical resistance of the material is insignificant since the material does not have to be electrically conductive and may therefore be high or low. Known materials are often more easily available and their chemical and thermal stability are known and/or optimized.

In accordance with an advantageous configuration, at least 20% of the first electrode consists of a metal. In further variants at least 50% or at least 95% of the electrode consists of a metal. A construction of 20%, 50% or 95% of a metal mixture or an alloy is therefore also possible. In a particularly advantageous configuration it is feasible for the electrode to consist completely of the metal or metal mixture or alloy. A particularly simple production as well as simple and cost-effective construction are therefore achieved, the electrical conductivity of the electrode optimally being very high. Examples of possible metals are gold or platinum, which are particularly suitable for applications at high temperatures. However, depending on the application other metals may also be used, such as aluminum or a tungsten/titanium alloy.

In accordance with one configuration it is also possible for the metal mixture to not be homogeneous, for example a metal being attached to a further metal, so as to ensure improved adhesion of the entire electrode for example. A further possibility for layered construction consists of the first electrode being provided with a material layer that impedes diffusion of foreign material, for example from the electrolyte.

In accordance with a further configuration it is particularly advantageous for the electrodes to consist of the same material. This makes it possible to achieve simpler production since, for example, both electrodes can be produced in a single processing step.

Alternatively however it is also possible to use different materials for the two electrodes. For example this may be advantageous if a material is used for the first electrode that impedes diffusion of foreign material, for example from the first catalytically active material. In this case the second electrode may be produced from a simpler or more cost-effective material.

A further advantageous configuration of the electrochemical gas sensor is obtained in that the sensor comprises at least a further first electrode. This is preferably covered, at least in part, by a further catalytically active material. Similarly to the first electrode it is also possible in this instance to provide one or more catalytic materials. It is therefore possible to determine and evaluate the relative voltages of a number of electrodes with respect to one another. This may lead to redundant and therefore secured signals or to additional information.

The voltage is therefore preferably determined between each of the first electrodes and the second electrodes and used as a measuring signal.

In accordance with a preferred configuration the first catalytically active material is selected so as to be different to the further catalytically active material. This means that the two or more first electrodes are in contact with each of the different catalytic materials. This makes it possible to obtain additional, independent measuring signals that, for example, afford more precise information regarding the gas composition. For example the concentrations of two gases may be ascertained from the signals of two electrodes, even if one or both electrodes react to both gases to some extent. An integrated sensor array, i.e. a multi-sensor arrangement, may therefore be formed with two or more first electrodes. The advantage of comparatively simple production and construction is also still achieved in this instance since, in this case also, the functions of electrical conductivity and catalytic activity are split between the electrode and the respective catalytically active material.

It is possible to construct the sensor so a second electrode, normally referred to as a reference electrode, is provided for each first electrode. However, the sensor preferably comprises just one second electrode since this makes it possible to save space and achieve simpler construction.

A first catalytically active material is preferably used that has a specific resistance of at least 1 μΩm at temperatures below 800° C. In further alternatives the material has a specific electrical resistance of less than 1 mΩm at temperatures below 800° C. or it has a specific electrical resistance of at least 1 μΩm or 1 mΩm at temperatures below 400° C.

A further configuration consists of the second electrode being covered, at least in part, by a second catalytically active material. This ultimately means that at least the first and second electrodes are constructed in a similar or identical manner. In this case it is not possible to distinguish between the electrodes by calling them an active and a passive electrode and instead the electrodes are equal. In this case the first catalytically active material is preferably different to the second catalytically active material. A gas signal is therefore made possible if both electrodes are in the measuring environment, i.e. are substantially subjected to the same gas mixture.

Alternatively however the same catalytic material may also be used. In this case it is expedient for the electrodes to be subjected to different gas environments, for example one of the electrodes being subjected to the ambient air and the other being subjected to the measuring gas environment.

In accordance with a further alternative the second electrode is covered, at least in part, by a protective material, in particular a perovskitic, ceramic or catalytic protective material. Increased chemical stability can thus be ensured.

In an advantageous configuration the first, second and/or further catalytic material comprises a SCR catalyst, for example a zeolite or a metal oxide, such as titanium oxide or vanadium oxide, or a $NO_x$ storage catalyst, such as platinum with barium. SCR catalysts are materials that are known per se and are used for selective catalytic reduction (SCR). They are known to be chemically and thermally stable and are therefore ideal. They can also be produced without difficulty.

In accordance with a further advantageous configuration the first, second and/or further catalytic material is porous and is therefore better penetrated by gas and thus has an improved sensor signal.

The electrochemical gas sensor preferably comprises a heating element. With planar construction of the sensor a heating element of this type may, for example, be configured as a heating meander, i.e. as an electric resistance heater. An alternative consists of a wire heating coil at which the sensor is formed, for example on a ceramic sheathing. It is also possible to provide more than one heating element. For example a heating element may be used for each first electrode. A further example consists of the sensor comprising a first and a second electrode and a heating element for each of the electrodes.

The heating element(s) heat the sensor, in particular so as to bring the catalytically active materials to an optimal operating temperature. In this case the optimal temperature depends on the type of material and the gas to be detected. In accordance with a further configuration it is therefore advantageous for the heater(s) to be configured and used in such a way that at least some of the electrodes can constantly be heated to different temperatures during operation. For example each of the electrodes may independently be kept at an individual, optimal temperature, which allows the sensor to be used in a highly versatile manner. In this case the temperatures for the electrodes preferably differ by at least 20° C., in particular by at least 100° C.

A shield, for example in the form of an equipotential layer between the heating element and the electrodes, may be provided between the heater and the electrodes in order to avoid the measurement being negatively influenced by the voltage drop in the heater.

The electrochemical gas sensor preferably comprises a temperature sensor, for example this sensor also possibly being formed as a single element, optionally with a heater, for example it may be formed as a platinum heating meander, In accordance with a further development it is particularly advantageous for a combined gas sensor to be created, wherein a resistive gas sensor is formed in addition to the electrochemical gas sensor. For this purpose at least a third electrode is provided in such a way that it is possible to determine the conductivity of the first catalytic material or that of the second or further catalytic material. The third electrode is therefore preferably in direct contact with the first, second or further catalytic material. In this case it is obviously expedient when measuring the first catalytic material for the third electrode to not simultaneously be in direct electrical contact with the first or second electrode.

It is therefore possible, in addition to the electrochemical measuring signal(s), to obtain a further, independent signal that, depending on the material, may correspond to that of a resistive gas sensor. It is particularly advantageous if the components normally required for a resistive sensor, such as heating or electric read-out systems, are formed with minimal effort or are already provided.

It is also possible to use two, separate, third electrodes to read out the electrical resistance. For example these may be configured as 'interdigital contacts', i.e. as finger-like or comb-like toothed contacts. This is particularly advantageous if the catalytic material exhibits a high electrical resistance since a reduced resistance is measured by the interdigital contacts.

It is also possible to produce a number of resistive gas sensors if a number of catalytically active materials are provided. In this case a difference in the sensitive properties of identical catalytically active materials may also be produced by the material of the underlying electrode, for example gold or platinum. At least a third electrode is therefore expediently provided for each of the catalytically active materials.

A further, alternative or additional, possible configuration consists of forming a 4-point measuring arrangement in order to determine the electrical resistance of the catalytic layers by a corresponding configuration of the third electrodes.

The third electrodes are preferably arranged, at least in part, on the first, second or further catalytically active material. Alternatively, one or more of the third electrodes may be arranged on the first or other electrodes and beneath the first or second or further catalytically active material, an electrically insulating, porous material preferably also being provided between these third electrodes and the first electrode.

The sensors described can advantageously be used in a sensor system. In one configuration a definable oxygen partial pressure may therefore also be set in at least some of the gas sensors, in each case in the region of at least one of the electrodes, for example the respective electrode being in contact with the ambient air whilst the other electrodes are in contact with the measuring gas.

Advantageous applications for the system or the sensor are:
in the exhaust gas system of a car or lorry, in particular in diesel motor vehicles, for example in order to detect ammonia during SCR or in order to detect other relevant gases,
in firing systems, power stations or gas turbines in order to detect exhaust gases,
in conjunction with catalysts, the state of which can be monitored with reference to the measuring results of the sensor or sensor system,
in lorries in order to detect ammonia, it being possible to establish whether sufficient urea or indeed any urea is present for SCR when there is an overdose of ammonia,
in order to detect ammonia when producing fertilizing agents,
in order to detect any leaks in cooling plants that use ammonia.

The main applications in these examples are ammonia detection; however the sensor is in no way limited to this. The gases that can be detected may advantageously be varied widely by appropriate selection of the catalytically active materials.

BRIEF DESCRIPTION OF THE DRAWINGS

Further advantages and details will be explained with reference to possible exemplary configurations illustrated in the drawings.

In this case FIGS. 1 and 2 are a plan view and a side view of an electrochemical gas sensor comprising two electrodes.

FIGS. 3 and 4 are again a plan view and a side view of an electrochemical gas sensor comprising three electrodes.

FIGS. 5 and 6 are a plan view and a side view of a combined electrochemical and resistive gas sensor.

Lastly, FIGS. 7 and 8 are a plan view and a side view of a combined electrochemical and resistive gas sensor.

DETAILED DESCRIPTION OF INVENTION

Figure 9:
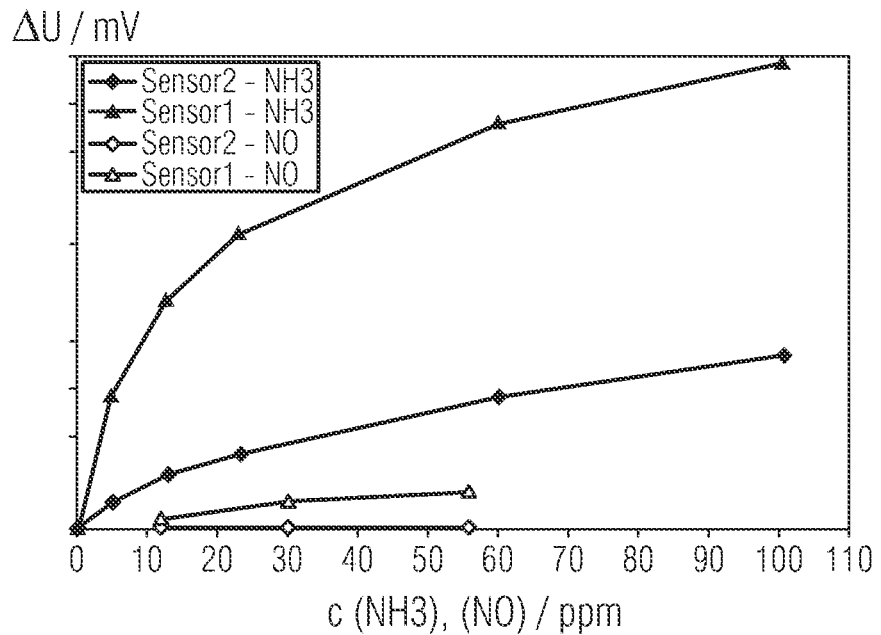
FIG. 9 is a schematic view of the dependency of the measuring signal of two catalytically active materials on the concentration of NO and $NH_3$.

With reference to FIGS. 1 and 2 an embodiment is shown schematically, FIG. 1 being a plan view of part of a first electrochemical gas sensor 10 and FIG. 2 being a view of the same sensor 10 from the front of the sensor. The first electrochemical sensor 10 is formed as a planar sensor, just as the further exemplary sensor variants 20, 30 and 40. This means that the main elements of the sensor are attached as layers to a ceramic substrate 1, the layers mostly being thin compared to their lateral extensions. It is also possible to produce sensors using non-planar technology. For example gas sensors are also produced effectively on small pipes made of aluminum oxide.

The first sensor variant 10 according to FIGS. 1 and 2 is assembled on a ceramic substrate 1. For example this substrate consists of aluminum oxide $Al_2O_3$. One side of the substrate, illustrated as the underside in FIG. 2, comprises a heating meander 12, in this case made of platinum. The other side of the ceramic substrate 1 comprises an electrolytic layer 2, for example made of yttrium-stabilized zirconium oxide, commonly referred to as YSZ. A first platinum electrode 4 and a second platinum electrode 3 are provided beside one another on the electrolytic layer 2. They project over the electrolytic layer 2 and are used to electrically tap the gas sensor 10 (this process not being shown in greater detail in the figures). The first platinum electrode 4 is coated with a catalyst layer 5 in the region of the electrolytic layer 2.

The first sensor variant 10 is therefore advantageously formed by a construction that is simple to produce by using two, for example completely similar, platinum electrodes 3, 4. A different reaction to different gases is achieved by the catalyst layer 5 on the first platinum electrode 4.

With reference to FIGS. 3 and 4 a second sensor variant 20 is shown schematically. In this case the second sensor variant 20 is configured so as to be similar in part to the first sensor variant 10 and the differences will be discussed hereinafter. Compared to the first sensor variant 10, the second sensor variant 20 comprises a further, third platinum electrode 6, the third platinum electrode 6 being coated by a further catalyst layer 7. It is expedient for the further catalyst layer 7 to consist of a different material to the catalyst layer 5. The third platinum electrode 6 and the first platinum electrode 4 can therefore advantageously be set so as to have different gas sensitivities, the second sensor variant 20 therefore being able to supply more information than the first sensor variant 10.

Figure 10:
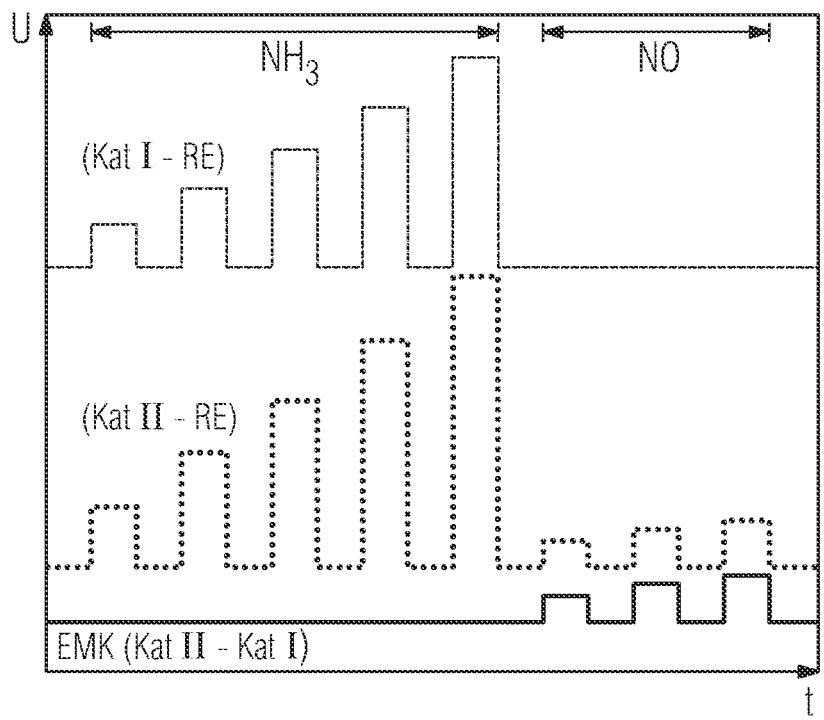
FIGS. 10 and 11 are schematic views of the progress over time of reactions of electrochemical and combined sensors to different concentrations of NO and $NH_3$.

In one exemplary embodiment a first catalyst is used that is sensitive to $NH_3$ and NO. The other first electrode comprises a second catalyst that merely reacts to $NH_3$. Signals can be obtained from the electrodes and these are shown schematically in FIG. 9. It can be seen that the second catalyst does not react to NO. The concentrations of NO and $NH_3$ can be determined by a suitable comparison of the measuring signals, for example a linear combination. In this regard FIG. 10 is a schematic view of the reaction, i.e. the measuring signal, that can be tapped at the electrodes for the two catalysts with the addition of different concentrations of NO and $NH_3$ in the vicinity of a gas sensor of this type.

With reference to FIGS. 5 and 6 a first combined sensor 30 is shown schematically. In this case the ceramic substrate 1 is not shown in FIG. 5 in order to provide a better overview.

Similarly to the first sensor variant 10, the first combined sensor 30 comprises a first and a second platinum electrode 3, 4, the first platinum electrode 4 in turn being covered by a catalyst layer 5. In contrast to the first sensor 10 however, the first combined sensor 30 comprises a first additional electrode 8, parts of which are arranged on the catalyst layer 5. Further electrical contact with the catalyst layer 5 is therefore created by the first additional electrode 8 in addition to the first platinum electrode 4. Changes in the electrical conductivity of the catalyst layer 5 may therefore be identified and tapped by the first platinum electrode 4 and the first additional electrode 8. These changes in conductivity may be used as a further measuring signal in addition to the electrochemical measuring signal that is tapped by the first and second platinum electrodes 3, 4. The catalyst layer 5 therefore acts as a resistive gas sensor in conjunction with the first additional electrode 8 and the first platinum electrode 4. If the catalyst layer 5 is a metal oxide layer then it is a resistive metal oxide gas sensor. The first combined sensor 30 is therefore a combination of an electrochemical gas sensor and a resistive gas sensor.

With reference to FIGS. 7 and 8 a further alternative for construction in the form of a second combined sensor 40 is shown schematically. The second combined sensor 40 now in turn comprises the first platinum electrode 4 with the catalyst layer 5 on the electrolytic layer 2. Alongside this a further catalyst layer 7 is now provided on the second platinum electrode 3. In this case it is expedient for the further catalyst layer 7 and the catalyst layer 5 to consist of different materials. A first additional electrode 8 and a second additional electrode 9 are provided so as to create a resistive gas sensor by way of the second combined sensor 40. These additional electrodes are arranged in part on the catalyst layer 5 and are configured as 'interdigital contacts' in the region of the catalyst layer 5. With the second combined sensor 40 the conductivity of the catalyst layer 5 is therefore determined with the first and second additional electrodes 8, 9. The first platinum electrode 4 does not have to participate in this.

It is advantageous for the further catalyst layer 7 to exhibit a high specific electrical resistance or for an insulating protective layer to be arranged over the second platinum electrode 3 instead of the further catalyst layer 7. In this case, as shown in FIG. 7, the second additional electrode 9 may, in this alternative configuration, extend over the two platinum electrodes 3 with the further catalyst layer 7 or the protective layer, without substantially distorting the measuring signals.

Figure 11:
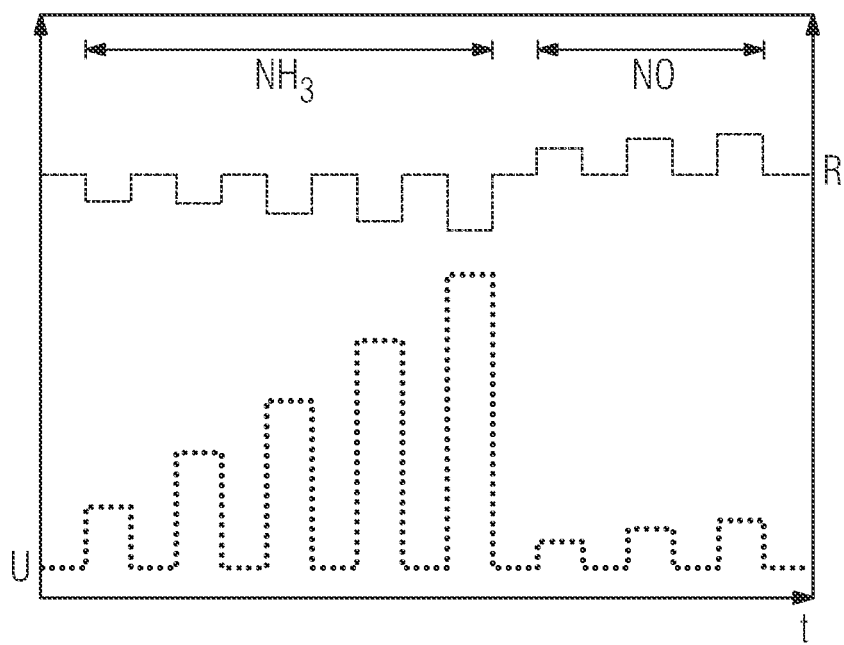

With reference to FIG. 11 the course of the signal for a combined gas sensor of this type is shown schematically. On the one hand the reaction of the voltage between the electrodes, i.e. the electrochemical signal, is shown and, on the other hand, the reaction of the conductivity of the catalyst, i.e. the resistive signal that is similar to that of a metal oxide gas sensor is shown. In this case also the concentrations of the target gases, for example in this instance NO and $NH_3$, can be determined by a suitable combination of the measuring signals, for example a linear combination.

Among the possible configurations that are given by the second sensor variant 20 and the second combined sensor 40, a particularly advantageous possible configuration consists of configuring the heating meander 12 in such a way that it heats the ceramic substrate 1 and therefore the respective sensor 20, 40 to a varying extent at different points. It is therefore possible for the different catalyst layers 5, 7 on the sensor to be at respective, different, optimal temperatures. An alternative consists of using a number of heating meanders that can be operated separately from one another. A further advantageous possible configuration, shown in this example in FIGS. 2, 6 and 8, consists of using an 'equipotential layer' 11. This expediently metal-conducting layer 11 is advantageously integrated into the ceramic substrate 1 in a planar manner and prevents the voltage, which drops across the heating meander 12, from having any influence on the voltage that can be tapped between the electrodes 3, 4, 6. It is also expedient for the heater 12 to be used simultaneously as a temperature sensor.

We claim:

1. Combined gas sensor, comprising:
    an electrochemical gas sensor formed by a first electrode and a second electrode,
        wherein the first and second electrodes are not in direct contact with one another but are connected via an ion-conducting material configured to allow a voltage to be formed as a first measuring signal between the first and second electrodes as a reaction to gases,
        wherein the first electrode is covered, at least in part, by a first catalytically active material,
    a resistive gas sensor formed by a third electrode such that the third electrode is in direct contact with the first catalytically active material and is not in direct contact with the first electrode, wherein the third electrode is configured to obtain a second measuring signal, the second measuring signal comprising a conductivity of the first catalytically active material.

2. Combined gas sensor according to claim 1, wherein at least 20% of the first electrode consists of a metal.

3. Combined gas sensor according to claim 1, wherein the first and second electrodes consist of the same material.

4. Combined gas sensor according to claim 1, comprising at least one further first electrode which is covered, at least in part, by a second catalytically active material.

5. Combined gas sensor according to claim 4, wherein the first catalytically active material is different from the second catalytically active material.

6. Combined gas sensor according to claim 1, wherein the first catalytically active material exhibits a specific resistance of at least 1 μΩm at temperatures below 800° C.

7. Combined gas sensor according to claim 1, wherein the second electrode is covered, at least in part, by a second catalytically active material.

8. Combined gas sensor according to claim 7, wherein the first catalytically active material is different from the second catalytically active material.

9. Combined gas sensor according to claim 7, wherein the first or second catalytically active material comprises an SCR catalytic converter or $NO_x$ storage catalytic converter.

10. Combined gas sensor according to claim 7, wherein the first or second catalytically active material is porous.

11. Combined gas sensor according to claim 1, wherein the second electrode is covered, at least in part, by a protective material.

12. Combined gas sensor according to claim 1, further comprising at least one heating element.

13. Combined gas sensor according to claim 12, wherein the at least one heating element is embodied such that the first and second electrodes are heated to different temperatures at the same time.

14. Combined gas sensor according to claim 12, further comprising an equipotential layer between the at least one heating element and the first and second electrodes.

15. Combined gas sensor according to claim 12, further comprising a temperature sensor.

16. Combined gas sensor according to claim 15, wherein the temperature sensor and the at least one heating element are formed as a single element.

17. Combined gas sensor according to claim 1, comprising a further third electrode, wherein the third electrodes are embodied as interdigital electrodes.

18. Combined gas sensor according to claim 17, wherein the third electrodes are arranged, at least in part, on the first catalytically active material.

19. Combined gas sensor according to claim 17, wherein one or more of the third electrodes are arranged on the first electrode and beneath the first catalytically active material, wherein an electrically insulating, porous material is provided between the third electrodes and the first electrode.

* * * * *